United States Patent
Dong et al.

(10) Patent No.: US 11,103,285 B2
(45) Date of Patent: Aug. 31, 2021

(54) PEDICLE SCREW ASSEMBLY FOR DYNAMIC AND STATIC FIXATION AND INSTALLATION TOOL THEREFOR

(71) Applicant: Xieping Dong, Jiangxi (CN)

(72) Inventors: Xieping Dong, Jiangxi (CN); Weiyi He, Guangdong (CN); Qingli Li, Jiangxi (CN); Yuanwei Zhang, Jiangxi (CN); Xiaoxiang Zhang, Jiangxi (CN); Xingliang Yu, Jiangxi (CN)

( * ) Notice: Subject to any disclaimer, the term of this patent is extended or adjusted under 35 U.S.C. 154(b) by 0 days.

(21) Appl. No.: 16/992,755

(22) Filed: Aug. 13, 2020

(65) Prior Publication Data
US 2021/0052305 A1 Feb. 25, 2021

Related U.S. Application Data

(63) Continuation of application No. PCT/CN2019/101617, filed on Aug. 20, 2019.

(51) Int. Cl.
*A61B 17/70* (2006.01)

(52) U.S. Cl.
CPC ...... *A61B 17/7037* (2013.01); *A61B 17/7005* (2013.01); *A61B 17/7032* (2013.01)

(58) Field of Classification Search
CPC ............ A61B 17/7032; A61B 17/7034; A61B 17/7035; A61B 17/7037; A61B 17/7041; A61B 17/8615
See application file for complete search history.

(56) References Cited

U.S. PATENT DOCUMENTS

| | | | | |
|---|---|---|---|---|
| 2011/0270325 | A1* | 11/2011 | Keyer | A61B 17/7007 606/305 |
| 2013/0072991 | A1* | 3/2013 | Rathbun | A61B 17/7041 606/305 |
| 2016/0183983 | A1* | 6/2016 | Heflin | A61B 17/7086 606/266 |

FOREIGN PATENT DOCUMENTS

| | | |
|---|---|---|
| CN | 101031248 A | 9/2007 |
| CN | 201492489 U | 6/2010 |
| CN | 201551382 U | 8/2010 |
| CN | 105934211 A | 9/2016 |
| CN | 109124749 A | 1/2019 |
| CN | 109788973 A | 5/2019 |
| WO | 2012142538 A1 | 10/2012 |

* cited by examiner

*Primary Examiner* — Julianna N Harvey

(57) ABSTRACT

There is provided a pedicle screw assembly for dynamic and static fixation, which is able to be assembled during the operation and allows a doctor to make an emergency choice between fusion fixation and non-fusion fixation. The pedicle screw assembly is used for inner fixation in spine surgery. During the operation, a pedicle screw is firstly implanted in a pedicle, and then a spherical head of the pedicle screw is enclosed by a connecting claw. After a screw seat is connected to the connecting claw by means of threads, a connecting rod is inserted in a groove and finally a locking screw is tightened to complete the fixation.

3 Claims, 11 Drawing Sheets

PEDICLE SCREW ASSEMBLY FOR DYNAMIC AND STATIC FIXATION AND INSTALLATION TOOL THEREFOR

CROSS-REFERENCE TO RELATED APPLICATIONS

This application is a continuation of International Patent Application No. PCT/CN2019/101617, filed on Aug. 20, 2019. The content of the aforementioned applications, including any intervening amendments thereto, is incorporated herein by reference in its entirety.

TECHNICAL FIELD

The present application relates to medical devices, particularly to human implants for orthopedics or neurosurgery, and more particularly to a pedicle screw assembly for dynamic and static fixation and an installation tool therefor.

BACKGROUND

The development of biomechanical research and material science broadens the application of the internal fixation technique. The existing pedicle screw fixation system used in orthopedic surgery generally includes several pedicle screws and a connecting rod that connects the pedicle screws. The pedicle screw includes a screw seat and a screw body which are connected and a locking screw.

During the operation, a tool is connected to the screw seat, so as to screw a screw body into pedicles of various spines, and then a connecting rod is connected to these screw seats of the pedicle screws located at the same side of the spines, and finally, the connecting rod is tightly fixed to the screw seats of these pedicle screws by the locking screws, which can strengthen the spines, thereby restoring a height of the spines which are compressed due to traumatic injury or lesions, or correcting deformed spines.

The pedicle screw system is divided into two types: rigid fusion fixation and flexible non-fusion fixation according to the conditions that the fixed segments are movable or not. The rigid fusion fixation has sufficient rigidity and can completely restrict the movement of the fixed segments, being a static fixation method. A pedicle screw having the function of the rigid fusion fixation is referred to as "a fixed screw". The flexible non-fusion fixation retains moderate flexion and extension between fixed segments, so as to reduce the stress concentration between adjacent segments, being a dynamic fixation method. A pedicle screw having the dynamic fixation mode is movable relative to the connecting rod after the fixation operation is completed, and thus is referred to as "a dynamic screw". However, these non-fusion dynamic screws have a large sized screw seat and too many pieces.

In addition, for the existing static pedicle screws and the existing dynamic pedicle screws, the screw seat and the screw body are assembled to be integrated before the operation. When these pedicle screws are implanted during the operation, it is difficult for doctors to accurately judge whether the implant reaches an appropriate depth, because the relatively small screw is covered by the large screw seat to make the observation of a neck of the screw difficult, which leads to undesired occurrences as follows. A screw tip can penetrate a front edge of the spine to endanger the large blood vessels when the implant is too deeply placed, or the implant has inadequate fixation strength due to a shallow implantation depth. In fact, these undesired occurrences are common in clinical practices and difficult to deal with. In the case of the shallow implantation depth, the fixation rod can be removed to screw the implant to the appropriate depth, which prolongs the operation time and increases the risk of bleeding and infection. In the case that the implant is too deeply placed, the dismantling of the implant also prolongs the operation time and increases the risk of bleeding and infection. In addition, unscrewing the pedicle screw will greatly reduce the fixation strength of a screw track and reduce the quality of the operation.

SUMMARY

The present application aims to provide a pedicle screw assembly for dynamic and static fixation and an installation tool therefor to solve the technical problems of the existing pedicle screws. In the present application, a pedicle screw and a screw seat of the pedicle screw are separated. Firstly, the pedicle screw is screwed in the pedicle to ensure the pedicle screw to be implanted at an appropriate position under the condition that the pedicle screw is not covered during the operation. Then a spherical head of the pedicle screw is snapped into a connecting claw which is connected to the screw seat, so as to complete the assembly of pedicle screw main bodies. Subsequently, a connecting rod is installed on the screw seat and all the pieces are fastened using locking screws, which is the same as the way of fixing the pedicle screw and the connecting rod in the exiting pedicle fixation system. Moreover, after the installation of the pedicle screw is completed, the doctor still can make a choice, during the operation, between a non-fusion fixation that can realize the flexible connection of the pedicle screw and the screw seat (at this time, the pedicle screw is dynamic) and a fusion fixation that can realize the rigid connection of the pedicle screw and the screw seat (at this time, the pedicle screw is fixed) according to clinical needs and the actual situation after intraoperative decompression and lesion removal. Moreover, the pedicle screw exposed outside the bone, i.e., the incisura of the pedicle screw, is sufficiently low, which can effectively reduce the pain and discomfort caused by the implant-induced stimulation on the paraspinal muscles.

The technical solutions of the present application are described as follows.

The present application provides a pedicle screw assembly for dynamic and static fixation. The pedicle screw assembly is claw-typed, hook-typed and cap-typed.

Specifically, provided herein is a pedicle screw assembly for dynamic and static fixation, comprising a screw seat, a connecting claw, a pedicle screw, a connecting rod and a locking screw;

wherein the connecting claw comprises an upper portion and a lower portion, which are integrated; the upper portion of the connecting claw is a hollow cylinder and is provided with an external thread on an outer surface of the upper portion of the connecting claw; the lower portion of the connecting claw is umbrella-shaped and is provided with a spherical cavity configured to match with a spherical head of the pedicle screw; the lower portion of the connecting claw is equally divided into a plurality of petals; each petal is able to unfold outward by an external force; and an annular groove is formed on an outer surface of an intersection of the upper portion and the lower portion of the connecting claw;

a groove is provided on the screw seat to let the connecting rod pass through the groove; the screw seat is provided with a hollow cavity; a lower end of the screw seat is provided with an umbrella-shaped opening, which matches with the lower portion of the connecting claw; an internal thread is provided at a lower portion of the hollow cavity of the screw seat to connect to the upper portion of the connecting claw;

the spherical head of the pedicle screw has a flat top, which is perpendicular to an axis of the pedicle screw; a blind hole is provided in a center of the flat top of the spherical head; the blind hole has a non-circular cross-section, which can be hexagonal, plum blossom-shaped and quadrilateral; and the blind hole is provided with an internal thread which matches with a screwdriver.

In some embodiment, the screw seat is hollow and cylindrical; the groove is U-shaped and provided at an upper portion of the screw seat; an upper portion of the hollow cavity of the screw seat is provided with an internal thread, which is configured to connect to the locking screw; and the locking screw is configured to lock the connecting rod.

In some embodiment, the spherical cavity of the lower portion of the connecting claw and the spherical head of the pedicle screw are in clearance fit or interference fit; when the spherical cavity and the spherical head are in clearance fit, the lower portion of the connecting claw flexibly fixes the spherical head; when the spherical cavity and the spherical head are in interference fit, the lower portion of the connecting claw rigidly fixes the spherical head.

In some embodiment, when the spherical cavity and the spherical head are in clearance fit, a width of the umbrella-shaped opening at the lower end of the screw seat is controlled to swing the pedicle screw within an angle of 10°.

In some embodiment, the clearance fit or interference fit between the spherical cavity and the spherical head depends on a height of the hook body or a diameter of the connecting rod.

In some embodiment, the lower portion of the connecting claw is equally divided into at least four petals.

In some embodiment, a hole is provided at a lower edge of an outer surface of each petal of the lower portion of the connecting claw.

Specifically, provided herein is a pedicle screw assembly for dynamic and static fixation, comprising a screw seat, a connecting claw, a pedicle screw and a connecting rod.

wherein the connecting claw comprises an upper portion and a lower portion, which are integrated; the upper portion of the connecting claw is a hollow cylinder and is provided with an external thread on an outer surface of upper portion of the connecting claw; the lower portion of the connecting claw is umbrella-shaped and is provided with a spherical cavity configured to match with a spherical head of the pedicle screw; the lower portion of the connecting claw is equally divided into a plurality of petals; each petal is able to unfold outward by an external force; and an annular groove is provided on an outer surface of an intersection of the upper portion and the lower portion of the connecting claw;

a groove is provided on the screw seat to pass through the connecting rod; the screw seat is provided with a hollow cavity; a lower end of the screw seat is provided with an umbrella-shaped opening, which matches with the lower portion of the connecting claw; an internal thread is provided at a lower portion of the hollow cavity of the screw seat to connect to the upper portion of the connecting claw;

the spherical head of the pedicle screw has a flat top, which is perpendicular to an axis of the pedicle screw; a blind hole is provided in a center of the flat top of the spherical head; and the blind hole is provided with an internal thread which matches with a screwdriver.

In some embodiment, the screw seat comprises a cylindrical body and a hook for holding the connecting rod; the cylindrical body and the hook are integrated; the hook protrudes from a side of the cylindrical body; and the hook is provided with a hook body to pass through the connecting rod.

In some embodiment, a recess is provided on an inclined surface of the lower portion of the connecting claw and is configured to cooperate with the hook body to lock the connecting rod.

In some embodiment, the spherical cavity of the lower portion of the connecting claw and the spherical head of the pedicle screw are in clearance fit or interference fit; when the spherical cavity and the spherical head are in clearance fit, the lower portion of the connecting claw flexibly fixes the spherical head; when the spherical cavity and the spherical head are in interference fit, the lower portion of the connecting claw rigidly fixes the spherical head.

In some embodiment, when the spherical cavity and the spherical head are in clearance fit, a width of the umbrella-shaped opening at the lower end of the screw seat is controlled to swing the pedicle screw within an angle of 10°.

In some embodiment, the clearance fit or interference fit between the spherical cavity and the spherical head depends on a height of the hook body or a diameter of the connecting rod.

In some embodiment, the lower portion of the connecting claw is equally divided into at least four petals.

In some embodiment, a hole is provided at a lower edge of an outer surface of each petal of the lower portion of the connecting claw.

Specifically, provided herein is a pedicle screw assembly for dynamic and static fixation, comprising a screw seat, a connecting claw, a pedicle screw, a connecting rod and a locking screw;

wherein the connecting claw comprises an upper portion and a lower portion, which are integrated; the upper portion of the connecting claw is a hollow cylinder and has a smooth outer surface; an internal thread is provided on an inner surface of the connecting claw; the lower portion of the connecting claw is umbrella-shaped and is provided with a spherical cavity configured to match with a spherical head of the pedicle screw; the lower portion of the connecting claw is equally divided into at least four petals; each petal is able to unfold outward by an external force; an annular groove is provided on an outer surface of an intersection of the upper portion and the lower portion of the connecting claw;

a groove is provided on the screw seat to pass through the connecting rod; a main body of the screw seat is hollow and cylindrical; the main body of the screw seat has a smooth inner surface; a hook is hook-shaped and sticks out from a side of the main body of the screw seat; the groove is provided in the hook body; and the main body of the screw seat and the hook are integrated;

an umbrella-shaped opening is provided at a lower end of the main body of the screw seat to match with the lower portion of the connecting claw; the screw seat is fixedly sleeved with the connecting claw via the locking screw; and the locking screw matches with the internal thread of the connecting claw;

the spherical head of the pedicle screw has a flat top, which is perpendicular to an axis of the pedicle screw; a blind hole is provided in a center of the flat top of the spherical head; and the internal thread is provided inside the blind hole to match with the screwdriver; and a recess is provided on an inclined surface of the lower portion of the connecting claw and is configured to cooperate with the hook body to lock the connecting rod.

In some embodiment, the spherical cavity of the lower portion of the connecting claw and the spherical head of the pedicle screw are in clearance fit or interference fit; when the spherical cavity and the spherical head are in clearance fit, a width of the umbrella-shaped opening at the lower end of the screw seat is controlled to swing the pedicle screw within an angle of 10°.

In some embodiment, the clearance fit or interference fit between the spherical cavity and the spherical head depends on a height of the hook body or a diameter of the connecting rod.

In some embodiment, the lower portion of the connecting claw is equally divided into at least four petals.

In some embodiment, a hole is provided at a lower edge of an outer surface of each petal of the lower portion of the connecting claw.

The present application further provides an installation tool for the pedicle screw assembly, comprising:

a screw implant tool for the pedicle screw;

a presser for pressing the connecting claw and the pedicle screw; and a cross screwdriver for threaded connection between the connecting claw and the screw seat;

wherein the screw implant tool comprises a tubular screwdriver having a screw core; a fine thread is provided at a bottom of the screw core and is configured to match with the internal thread of the blind hole; a first joint is provided at a top of the screw core to connect to a core handle; the core handle and the screw core are detachably connected; a bottom of the tubular screwdriver is provided with a connector which adapts to a shape of the blind hole; a second joint is provided at a top of the tubular screwdriver to connect to a tubular screwdriver handle; and the tubular screwdriver handle and the tubular screwdriver are detachably connected;

the presser is able to rotate around an axial direction of the tubular screwdriver and move along the axial direction of the tubular screwdriver; and the presser is able to push the connecting claw to engage with the spherical head in a snap fit; and the cross screwdriver is hollow and cylindrical and is sleeved on the tubular screwdriver; the cross screwdriver is able to rotate around the axial direction of the tubular screwdriver; at least two rotating handles are fixedly provided in an outer surface of a top of the cross screwdriver; and an outer surface of a bottom of the cross screwdriver is fixedly provided with a protrusion which matches with a cross groove in the connecting claw.

The present application has the following beneficial effects.

1) Comparing to the existing pedicle screw having a large-sized screw seat, in the present application, the screw implantation depth can be clearly distinguished when the tiny pedicle screw is screwed in a vertically downward direction, thereby ensuring the surgical safety and efficiency and fixation quality during the implantation of the screw.

2) In the present application, after the screw is implanted, the doctor can decide whether to modify the preoperative plan by comprehensively considering various factors, such as, lesion status observed during the operation, whether the spinal canal is decompressed and the status of the spinal decompression, whether the structural integrity of the facet joint is damaged, the firmness of the screw implantation, the stability of the fixed segments, and the activity requirements after the surgery. Such that, the static fixation system that is conducive to bone fusion of the fixed segments or the non-fusion fixation system that allows moderate dynamic movement of the fixed segments can be finally determined. However, the existing integrated pedicle screw cannot be adjusted after the implantation, failing to meet various fixation requirements according to intraoperative situation.

3) The pedicle screw exposed outside the bone, i.e., the incisura of the pedicle screw, is much lower than the existing pedicle screw, which can effectively reduce the pain and discomfort caused by the implant-induced stimulation on the paraspinal muscles, which is particularly important for the physically weak patients and the patients with thoracolumbar kyphosis and effectively reduces the occurrence of the local pressure sores.

4) Compared to the existing pedicle screw, the pedicle screw assembly and the pedicle screw assembly in the present application have a significant advantage, that is, the nut that matches with the locking screw is annular with complete thread. While the existing pedicle screw has a U-shaped screw seat, which expands and thus becomes ineffective when the locking screw is over-tightened.

Figure 1:
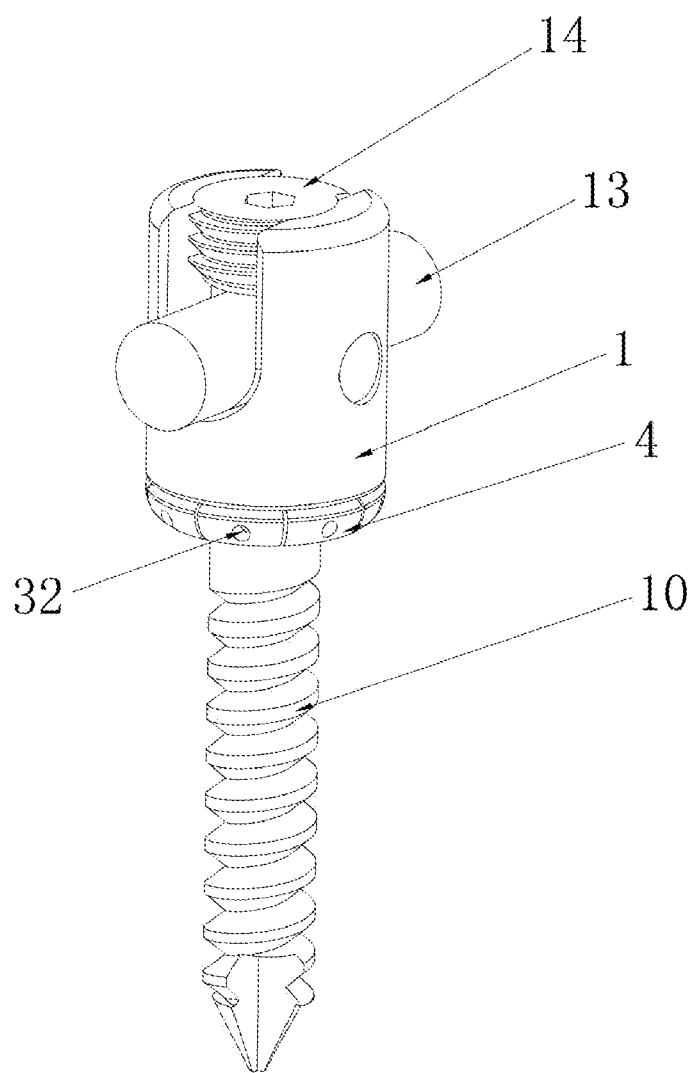
FIG. 1 is a perspective view of a pedicle screw assembly for dynamic and static fixation according to at least one embodiment of the present application.

In the drawings: 1, screw seat; 2, groove; 3, umbrella-shaped opening; 4, connecting claw; 5, upper portion; 6, lower portion; 7, spherical cavity; 8, petal; 9, annular groove; 10, pedicle screw; 11, spherical head; 12, blind hole; 13, connecting rod; 14, locking screw; 15, cylindrical body; 16, hook; 17, hook body; 18, inclined surface; 19, recess; 20, claw tip; 21, gap; 22, screw core; 23, bottom; 24, middle rear part; 25, top; 26, tubular screwdriver; 27, tubular screwdriver handle; 28, core handle; 29, presser; 30, cross screwdriver; 31, cross screwdriver handle; 32, hole; and 33, cross groove.

DETAILED DESCRIPTION OF EMBODIMENTS

The present application will be further described in detail below with reference to the embodiments to clearly explain the technical problems to be solved, the technical solutions and the beneficial effects. It should be understood that the embodiments disclosed herein are merely illustrative and are not intended to limit the present application.

In the description of the present application, the terms "left", "right" and the like refer to the orientation or positional relationship shown in the drawings shown, which are merely for better description of the present disclosure and do not require that the present application must be in specific positional configuration with specific operations. They are not intended to limit the present application.

Embodiment 1

Figure 2:
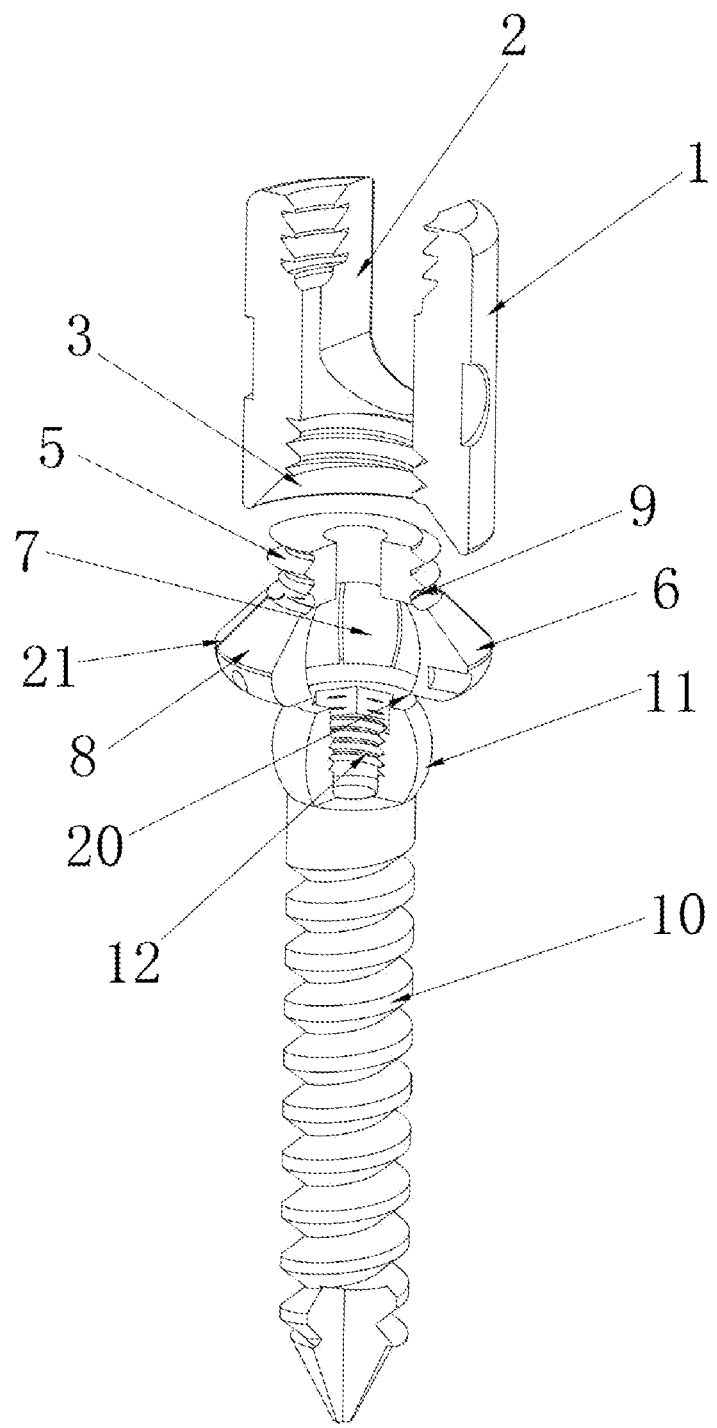
FIG. 2 is an exploded view of the pedicle screw assembly according to at least one embodiment of the present application.

Provided herein is a pedicle screw assembly for dynamic and static fixation, as shown in FIGS. 1 and 2. The pedicle screw assembly includes a screw seat 1, a connecting claw 4 and a pedicle screw 10. The connecting claw 4 includes an upper portion 5 and a lower portion 6, which are integrated. An external thread is provided on an outer surface of the upper portion of the connecting claw 4. The lower portion 6 of the connecting claw is provided with a spherical cavity 7, which is configured to match with a spherical head 11 of the pedicle screw 10. The lower portion 6 of the connecting claw is equally divided into a plurality of petals 8 which are able to unfold outward by an external force. An annular groove 9 is provided on an outer surface of an intersection of the upper portion and the lower portion of the connecting claw.

A groove 2 is provided on the screw seat 1 to pass through a connecting rod 13. The screw seat 1 is provided with a hollow cavity hollow. An umbrella-shaped opening 3 is provided at a lower end of the screw seat 1 to match with the lower portion 6 of the connecting claw. An internal thread is provided at a lower portion of the hollow cavity of the screw seat 1 and is connected to the upper portion of the connecting claw 4.

The spherical head 11 of the pedicle screw 10 has a flat top, which is perpendicular to an axis of the pedicle screw 10. A blind hole 12 is provided in a center of the flat top of the spherical head to engage with a screwdriver. The blind hole has a non-circular cross-section, which can be hexagonal, plum blossom-shaped and quadrilateral. An internal thread is provided inside the blind hole 12 to fix the screwdriver.

In the present embodiment, the screw seat 1 is hollow and cylindrical. The groove 2 of the screw seat 1 is U-shaped and provided at an upper portion of the screw seat 1. An internal thread is provided at an upper portion of the hollow cavity of the screw seat 1 to connect to a locking screw 14. The locking screw 14 is configured to compress the connecting rod 13.

In the present embodiment, the spherical cavity 7 of the lower portion 6 of the connecting claw and the spherical head 11 of the pedicle screw 10 are in clearance fit or interference fit.

In the present embodiment, when the spherical cavity 7 of the lower portion 6 of the connecting claw and the spherical head 11 of the pedicle screw 10 are in clearance fit, a width of the umbrella-shaped opening 3 at the lower end of the screw seat 1 is controlled to swing the pedicle screw 10 within an angle of 10°.

In the present embodiment, the lower portion 6 of the connecting claw is equally divided into at least four petals.

In order to apply the pedicle screw assembly in clinical practices, the present application further provides an installation tool for the pedicle screw assembly, which includes a screw implant tool for the pedicle screw 10 and a presser 29 screwed to an outer wall of the screw implant tool for pressing the connecting claw 4 and the pedicle screw 10.

Figure 9:
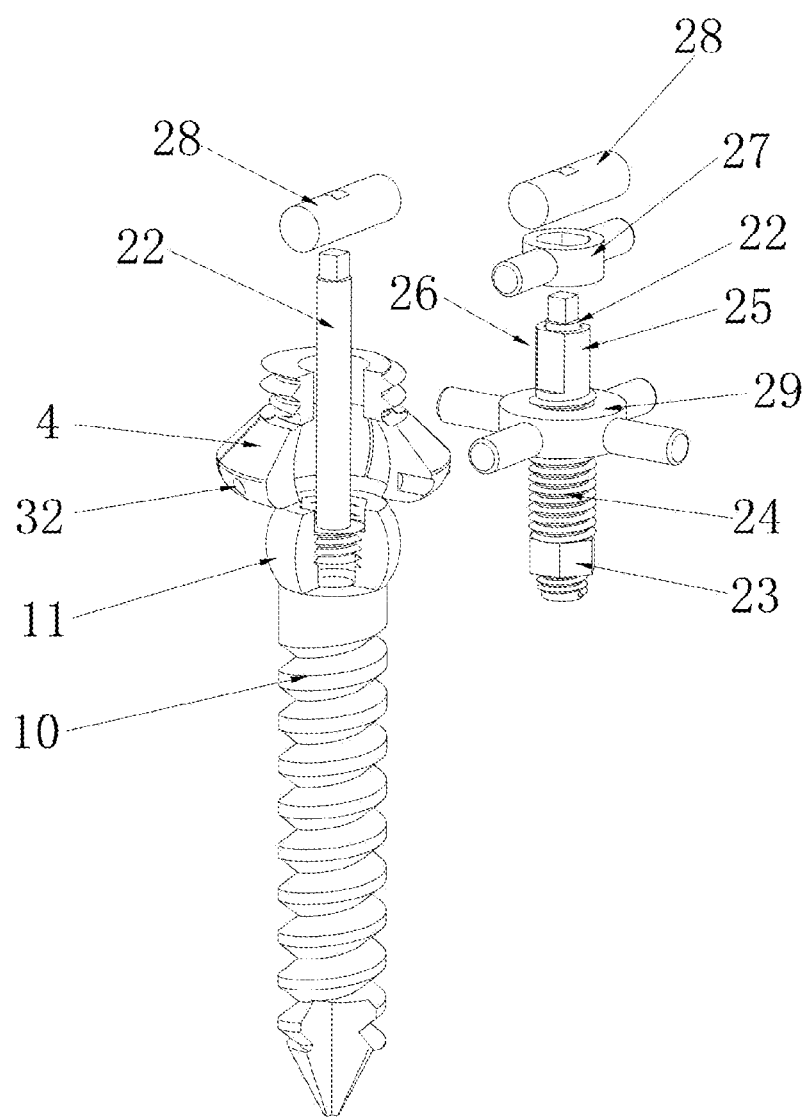
FIG. 9 is a perspective view of an installation tool for implanting screw and pressing a connecting claw and a pedicle screw according to at least one embodiment of the present application.

During the operation, a specialized screw implant tool, as shown in FIG. 9, connects a specialized blind hole 12 of the pedicle screw 10 to implant the pedicle screw 10 in a pedicle of a corresponding spine. The blind hole 12 matches with a screwdriver and will be explained in detail below. In the process of implanting the pedicle screw, the pedicle screw is not covered by the screw seat. While in the existing pedicle screw, the pedicle screw is covered by the screw seat. Therefore, the pedicle screw of the present application can be accurately implanted at an appropriate position by an operator.

When the pedicle screw 10 is accurately implanted in the pedicle, a handle of the screw implant tool is removed, and then the connecting claw 4 is inserted into the screw implant tool to touch the spherical head 11 of the pedicle screw 10. When an opening at a lower end of the connecting claw 4 is in a natural state, a diameter of the opening at the lower end of the connecting claw 4 is smaller than an outer diameter of the spherical head 11, the connecting claw 4 fails to engage with the spherical head 11 in a snap fit.

Subsequently, a press-fitting tool is installed on the screw implant tool to press the connecting claw 4 and the pedicle screw 10. The press-fitting tool includes the screw implant tool and a presser 29 screwed to the outer wall of the screw implant tool. The presser 29 is rotated to reach a top surface of the connecting claw 4. Since the connecting claw 4 is provided with the annular groove 9 and the lower portion 6 of the connecting claw is equally divided into the plurality of petals 8, the continuous rotation of the presser 29 can gradually unfold the petals 8 outward and gradually enlarge the opening at the lower end of the connecting claw 4. When the diameter of the opening at the lower end of the connecting claw 4 is larger than the maximum outer diameter of the spherical head 11, the opening of the connecting claw 4 can enclose the spherical head 11 to realize the snap fit between the connecting claw 4 and the spherical head 11.

It can be seen from the above operation that it is essential to design the annular groove 9 and the number of the petals 8 due to their influence on the intensity of the required force applied downward. Through experiments, it is found that the lower portion 6 of the connecting claw is preferably equally divided into eight petals.

A claw tip 20 of the connecting claw 4 is preferably designed to have a certain arc, which benefits the claw tip 20 to move along a spherical surface of the spherical head 11. When the claw tip 20 reaches the maximum outer diameter of the spherical head 11, the lower portion 6 of the connecting claw expands to the maximum. At this time, a gap 21 between two adjacent petals is also enlarged. However, when the force applied to the connecting claw 4 continues to be increased, the connecting claw 4 continues to move downward, and then the claw tip 20 passes through the maximum outer diameter of the spherical head 11, at this time, the resistance acting on the claw tip 20 is drastically reduce, and the lower portion 6 of the connecting claw springs back into its original shape to enclose the spherical head 11 in the spherical cavity 7 of the connecting claw 4.

Next, the screw seat 1 and the connecting claw 4 are screwed. The umbrella-shaped opening 3 abuts against an umbrella-shaped surface of the lower portion 6 of the connecting claw to prevent the lower portion 6 of the connecting claw from unfolding outward, so that the spherical head 11 is limited to swinging in the spherical cavity 7.

In the present embodiment, a hole 32 is provided at a lower edge of an out surface of the connecting claw 4 to allow the screw seat 1 and the connecting claw 4 to be tightly screwed, specifically, a plier of the screwdriver is stuck at the hole 32 to increase a holding force of screwing the connecting claw 4. Specifically, the hole 32 is a circular blind hole located at the lower edge of the out surface of each petal 8.

In the present embodiment, the spherical cavity 7 and the spherical head 11 are in clearance fit, that is, the lower portion 6 of the connecting claw flexibly fixes the pedicle screw 10, and the pedicle screw can relatively swing within a range of 10°, which are the main features of the dynamic screw in the non-fusion fixation.

In the present embodiment, the spherical cavity 7 and the spherical head 11 are in interference fit, that is, the lower portion 6 of the connecting claw rigidly fixes the pedicle screw 10, and the pedicle screw 10 and the connecting rod 13 are also rigidly fixed, which are the main features of the fixed screw in the fusion fixation of rigid connection.

In other words, the connecting claw 4 of present embodiment has a dual mode, that is, the connecting claw 4 and the pedicle screw 10 are in clearance fit or in interference fit. Due to such dual mode, after the pedicle screw 10 is implanted in the pedicle, the doctor still can modify the plan according to the needs during the operation and decide whether the dynamic screw or the fixed screw is finally used, greatly facilitating the clinical practices of the pedicle screw.

Finally, a universal connecting rod 13 is provided in grooves 2 of screw seats 1 which are placed in adjacent pedicles on the same side of the spine, and then the connecting rod 13 and the screw seat 1 are locked by a locking screw 14, thereby completing the whole installation process.

Embodiment 2

Figure 3:
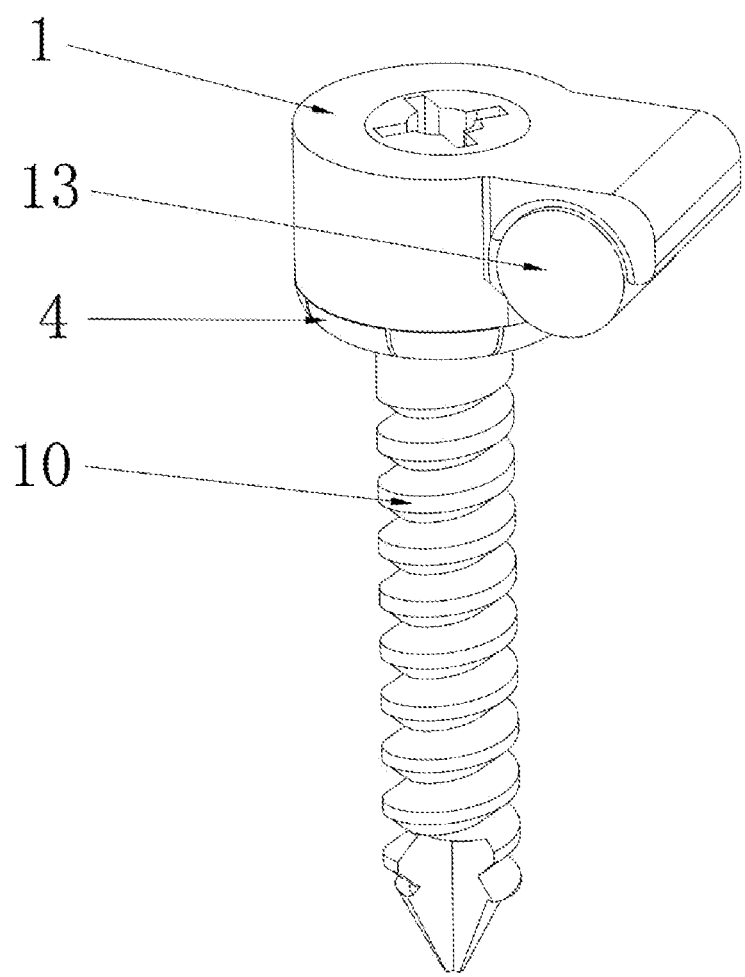
FIG. 3 is a perspective view of a pedicle screw assembly for dynamic and static fixation according to at least one embodiment of the present application.
Figure 4:
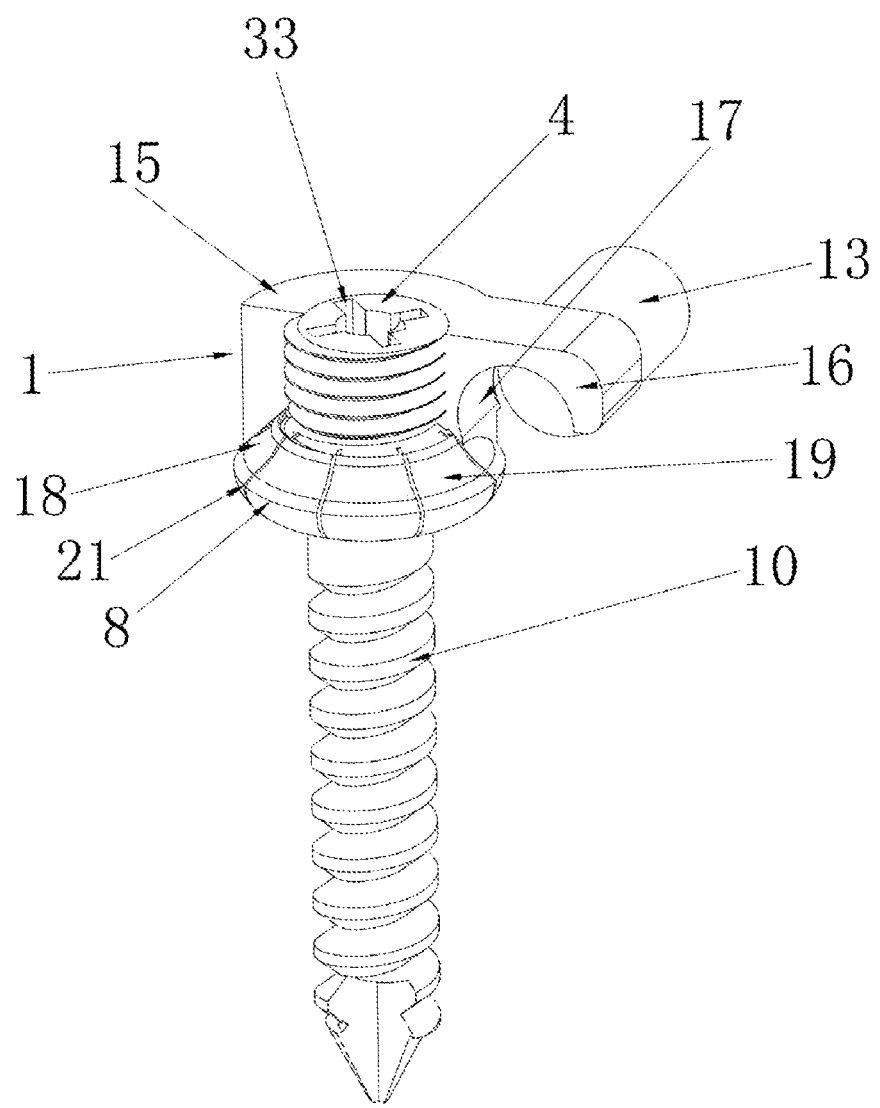
FIG. 4 is a partial exploded view of the pedicle screw assembly according to at least one embodiment of the present application.
Figure 5:
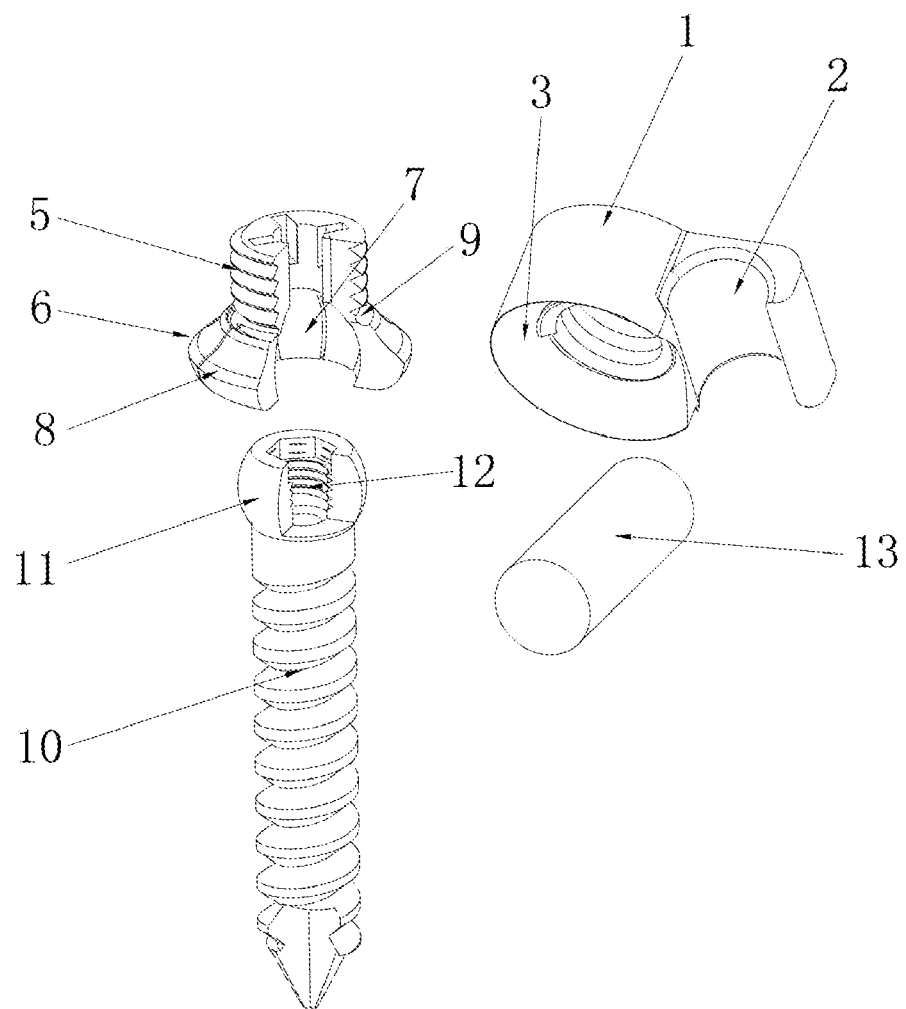
FIG. 5 is an exploded view of the pedicle screw assembly according to at least one embodiment of the present application.

As shown in FIGS. 3-5, Embodiment 2 differs from Embodiment 1 in that the screw seat 1 has a different structure, and the locking screw 14 is not used to press the connecting rod 13, such that fewer parts are used to compact the structure of the pedicle screw in the present embodiment.

Specifically, provided herein is a pedicle screw assembly for dynamic and static fixation, including a screw seat 1, a connecting claw 4 and a pedicle screw 10. The connecting claw 4 includes an upper portion 5 and a lower portion 6, which are integrated. The upper portion 5 of the connecting claw 4 is a hollow cylinder and is provided with an external thread on an outer surface of the upper portion of the connecting claw 4. The lower portion 6 of the connecting claw is umbrella-shaped and is provided with a spherical cavity 7 configured to match with a spherical head 11 of the pedicle screw 10. The lower portion 6 of the connecting claw is equally divided into a plurality of petals 8 which are able to unfold outward by an external force. An annular groove 9 is provided on an outer surface of an intersection of the upper portion and the lower portion of the connecting claw.

A groove 2 is provided on the screw seat 1 to pass through a connecting rod 13. The screw seat 1 is provided with a hollow cavity. An umbrella-shaped opening 3 is provided at a lower end of the screw seat 1 to match with the lower portion 6 of the connecting claw. An internal thread is provided at a lower portion of the hollow cavity of the screw seat 1 to connect to the upper portion of the connecting claw 4.

The spherical head 11 of the pedicle screw 10 has a flat top, which is perpendicular to an axis of the pedicle screw 10. A blind hole 12 is provided in a center of the flat top of the spherical head to engage with a screwdriver. An internal thread is provided inside the blind hole 12 to fix the screwdriver.

In the present embodiment, the screw seat 1 includes a cylindrical body 15 and a hook 16 for holding the connecting rod. The hook protrudes from a side of the cylindrical body 15. The cylindrical body 15 and the hook 16 are integrated. The hook 16 is provided with a hook body 17 to pass through the connecting rod.

In this embodiment, a recess 19 is provided on an inclined surface 18 of the lower portion 6 of the connecting claw 4 and is configured to cooperate with the hook body 17 to lock the connecting rod 13.

In this embodiment, a screwdriver joint is provided at an upper end of an inner cavity of the connecting claw 4. The screwdriver joint herein is, for example, a cross groove 33.

In the present embodiment, the spherical cavity 7 of the lower portion 6 of the connecting claw and the spherical head 11 of the pedicle screw 10 are in clearance fit or interference fit.

In the present embodiment, when the spherical cavity 7 of the lower portion 6 of the connecting claw and the spherical head 11 of the pedicle screw 10 are in clearance fit, a width of the umbrella-shaped opening 3 at the lower end of the screw seat 1 is controlled to swing the pedicle screw 10 within an angle of 10°.

In the present embodiment, the lower portion 6 of the connecting claw is equally divided into at least four petals.

In this embodiment, the way of realizing the dual mode of the fixation and movement is the same as the way in Embodiment 1, that is, the dual mode is realized by controlling the way that the connecting claw 4 engages with the spherical head 11. While the way of realizing the dual mode of the fixation and movement can be different from the way in Embodiment 1, that is, the dual mode is realized by keeping the way that the connecting claw 4 engages with the spherical head 11 while changing a height of the hook body 17 or a diameter of the connecting rod 13, so as to choose the flexible fixation or the rigid fixation.

In order to apply the pedicle screw assembly in clinical practices, the present application further provides an installation tool for the pedicle screw assembly that includes a screw implant tool for the pedicle screw 10, a presser 29 screwed to an outer wall of the screw implant tool for pressing the connecting claw 4 and the pedicle screw 10, and a cross screwdriver 30 sleeved on an outer wall of the tubular screwdriver 26 for threaded connection between the connecting claw 4 and the screw seat 1.

The cross screwdriver 30 is hollow and cylindrical and has a smooth inner surface. At least two rotating handles are fixedly provided in an outer surface of a top of the cross screwdriver 30. An outer surface of a bottom of the cross screwdriver 30 is fixedly provided with a protrusion which matches with the cross groove 33 in the connecting claw 4.

During the operation, firstly, the pedicle screw 10 is implanted in a pedicle of a corresponding spine by screwing the specialized screw implant tool in the blind hole 12 that is specialized for the screwdriver. In the process of implanting the pedicle screw, the pedicle screw is not covered by the screw seat that is different from the existing screw seat. Therefore, the pedicle screw of the present application can be accurately implanted in place by an operator.

When the pedicle screw 10 is accurately implanted into the pedicle, the operator only requires a specialized installation tool as shown in FIG. 9 to press the connecting claw 4 and the pedicle screw 10. The presser 29 on the specialized installation tool is rotated to realize the snap fit between the connecting claw 4 and the spherical head 11.

After the snap fit between the connecting claw 4 and the spherical head 11 is completed, a core handle 28, a tubular screwdriver handle 27 and the presser 29 are sequentially removed. Then the tubular screwdriver 26 is inserted into the screw seat 1 provided with the groove 2 at a side of the screw seat 1 to arrive at a top of the connecting claw 4. Next, the cross screwdriver 30 is sleeved on the tubular screwdriver 26, and the protrusion of the cross screwdriver 30 is inserted into the cross groove 33 of the connecting claw 4. When the cross screwdriver 30 is rotated to raise an upper edge of the connecting claw 4 to a middle of the screw seat 1 (in fact, the screw seat 1 is pressed downward), the connecting rod 13 is placed in the groove 2. The cross screwdriver 30 continues to rotate, and the connecting rod 13 will abut against the inclined surface 18 of the lower portion 6 of the connecting claw 4, so that the connecting rod 13 is restrained by the hook body 17 to be fastened.

At the same time, the umbrella-shaped opening 3 has a gap at the hook body 17, and a lower edge of the connecting rod 13 can supplement such gap to restore the approximately circular constraint. Thus, the petals of the lower portion 6 of the connecting claw gather inward to reduce the gap between adjacent petals and diminish the spherical cavity 7, thereby restraining the spherical head 11 and preventing the pedicle screw 10 from falling off. When the flexible fixation is chosen, a connecting claw 4 or a screw seat 1 which can allow the spherical cavity 7 and the spherical head 11 to be in clearance fit is used for assembly. When the static fixation is chosen, a connecting claw 4 or a screw seat 1 which can allow the spherical cavity 7 and the spherical head 11 to be in interference fit is used for assembly.

In this embodiment, the connecting rod 13 functions better in preventing the pedicle screw 10 from falling off when a diameter of the connecting rod 13 is 6 mm, and the effective containment arc of the hook body 17 is 180°, and the recess 19 has a depth of 0.5 mm. The pedicle screw of the present application has a better fixed connection between the screw seat 1 and the upper portion of the connecting claw 4 than the existing pedicle screw, because in the exiting pedicle screw, the U-shaped opening readily expands outward to cause the failure of the locking screw when the locking screw is over-tightened. While in the present application, such failure is completely avoided.

Embodiment 3

Figure 6:
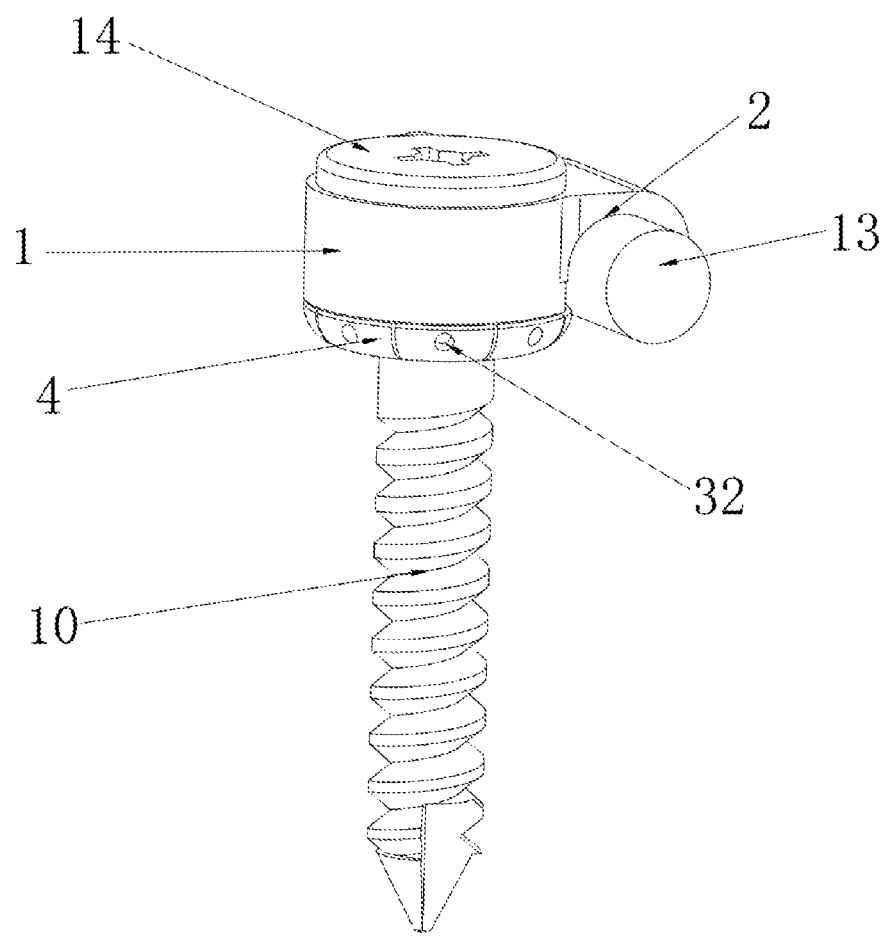
FIG. 6 is a perspective view of a pedicle screw assembly for dynamic and static fixation according to at least one embodiment of the present application.
Figure 7:
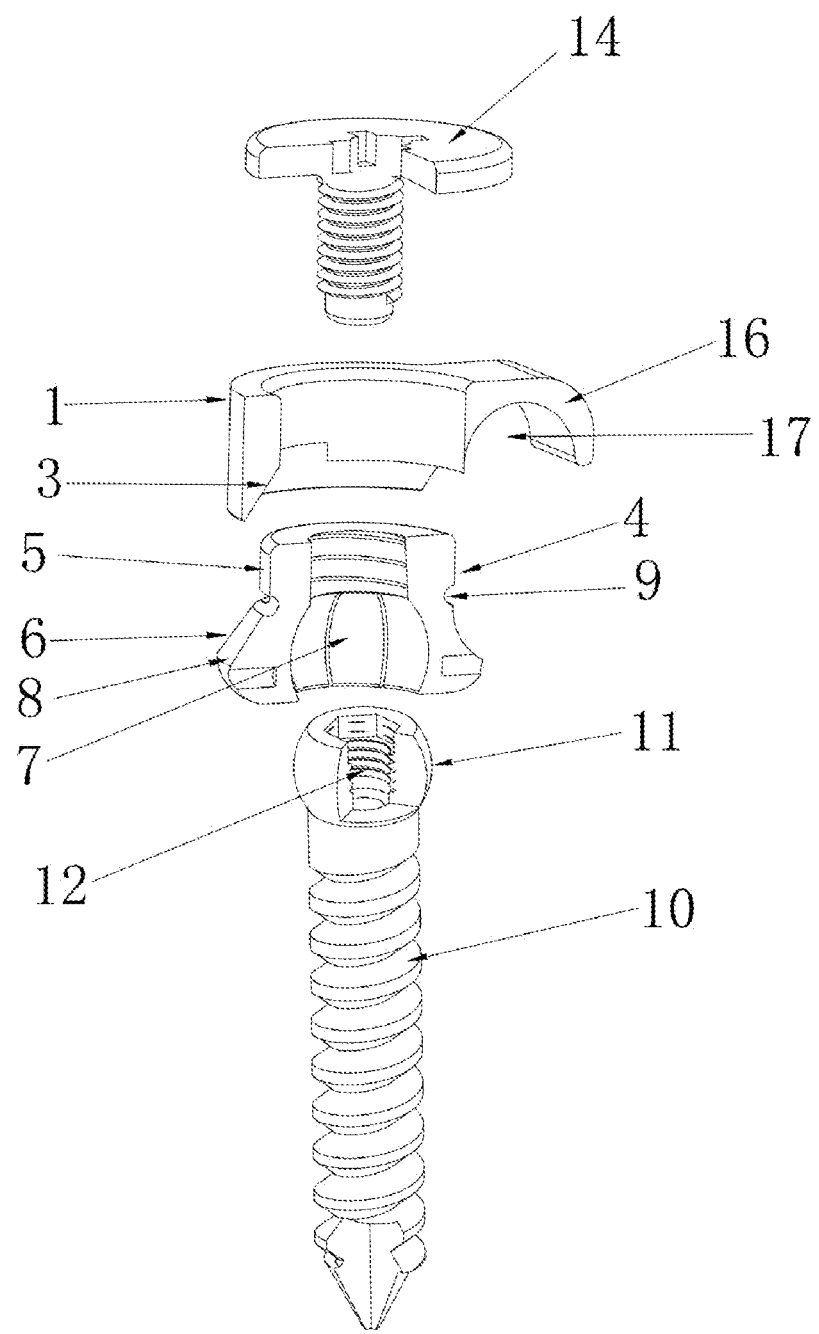
FIG. 7 is an exploded view of the pedicle screw assembly according to at least one embodiment of the present application.
Figure 8:
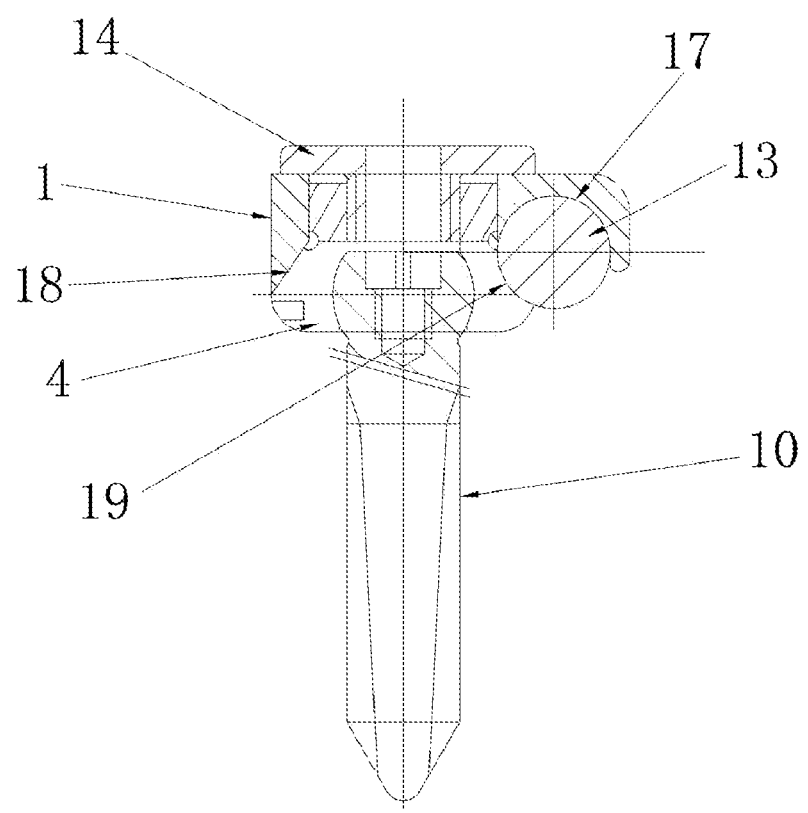
FIG. 8 is a cross-sectional view of the pedicle screw assembly according to at least one embodiment of the present application.

As shown in FIGS. 6-8, Embodiment 3 differs from Embodiment 2 in that the screw seat 1 and the connecting claw 4 are no longer in threaded connection. An inner thread is additionally provided in an inner surface of the upper portion of the connecting claw 4. Moreover, the connecting claw 4, the screw seat 1 and the connecting rod 13 are locked together by a cap locking screw 14. Such design facilitates the operation, and the pieces used herein has a low precision requirement of the manufacture.

Specifically, provided herein is a pedicle screw assembly for dynamic and static fixation, including a screw seat 1, a connecting claw 4 and a pedicle screw 10. The connecting claw 4 includes an upper portion 5 and a lower portion 6, which are integrated. The upper portion 5 is a hollow cylinder and has a smooth outer surface. An internal thread is provided on an inner surface of the upper portion 5 of the connecting claw. The lower portion 6 of the connecting claw is umbrella-shaped and is provided with a spherical cavity 7 configured to match with a spherical head 11 of the pedicle screw 10. The lower portion 6 of the connecting claw is equally divided into a plurality of petals which are able to open outward by an external force. An annular groove 9 is provided on an outer surface of an intersection of the upper portion and the lower portion of the connecting claw.

A groove 2 is provided on the screw seat 1 to pass through a connecting rod 13. A main body of the screw seat 1 is hollow and cylindrical. The main body of the screw seat 1 has a smooth inner surface. A hook 16 is hook-shaped and protrudes from a side of the main body of the screw seat 1. The hook is provided with a hook body 17. The main body of the screw seat 1 and the hook 16 are integrated.

An umbrella-shaped opening 3 is provided at a lower end of the main body of the screw seat 1 to match with the lower portion 6 of the connecting claw. The screw seat 1 is fixedly sleeved with the connecting claw 4 via a locking screw 14. The locking screw 14 matches with the internal thread of the connecting claw. The locking screw 14 is a cap-shaped locking screw.

The spherical head 11 of the pedicle screw 10 has a flat top, which is perpendicular to an axis of the pedicle screw 10. A blind hole 12 is provided in a center of the flat top of the spherical head to engage with a screwdriver. An internal thread is provided inside the blind hole 12 to fix the screwdriver.

A recess 19 is provided on an inclined surface 18 of the lower portion 6 of the connecting claw 4 and is configured to cooperate with the hook body 17 to lock the connecting rod 13.

In this embodiment, a hole 32 is provided at a lower edge of an outer surface of the connecting claw 4 to tightly connect the screw seat 1 and the connecting claw 4, specifically, a plier of the screwdriver is stuck at the hole 32 to increase a holding force of screwing the connecting claw 4. Specifically, the hole 32 is a circular blind hole located at the lower edge of the out surface of each petal 8.

In order to apply the pedicle screw assembly in clinical practices, the present application further provides an installation tool for the pedicle screw assembly, which includes a screw implant tool for the pedicle screw 10, a presser 29 screwed to an outer wall of the screw implant tool for pressing the connecting claw 4 and the pedicle screw 10.

During the operation, the steps of implanting the pedicle screw 10 and installing the connecting claw 4 are the same as the steps in Embodiment 2. The difference between Embodiment 2 and Embodiment 3 is that the screw seat 1, the connecting claw 4 and the connecting rod 13 are fixed by the cap locking screw 14 in Embodiment 3, while the screw seat 1 and the connecting claw 4 are in threaded connection in Embodiment 2.

Figure 10:
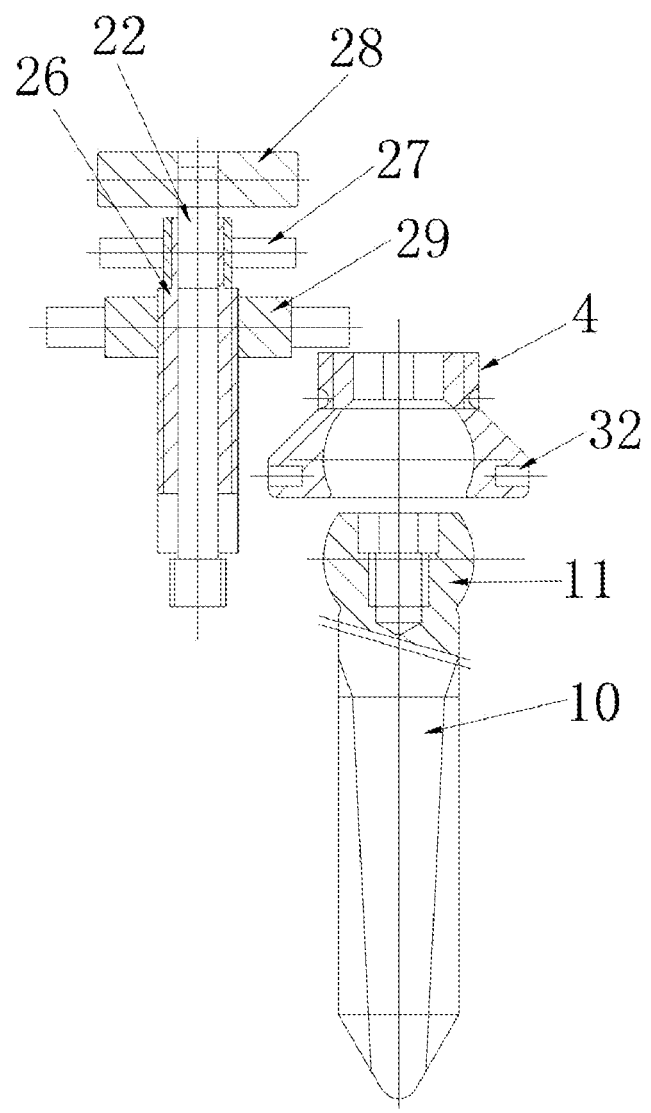
FIG. 10 is a cross-sectional view of the installation tool in FIG. 9.
Figure 11:
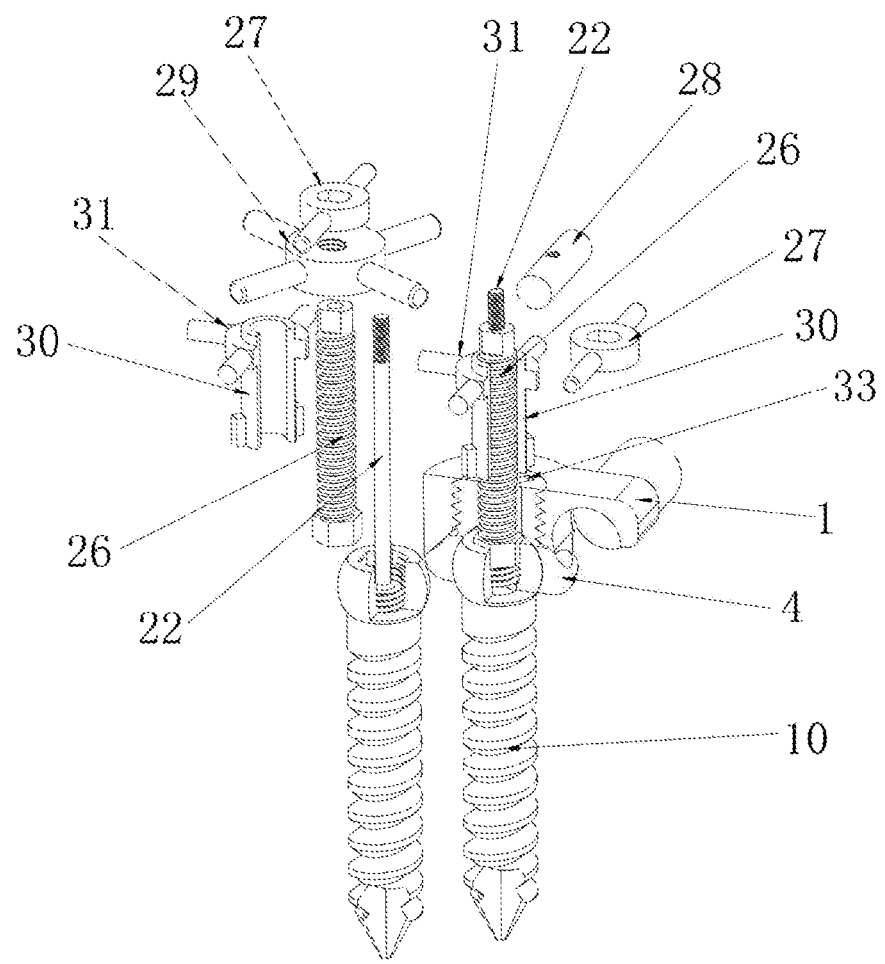
FIG. 11 is a perspective view of an installation tool for connecting the connecting claw and the screw seat according to at least one embodiment of the present application.

In order to facilitate the operation and ensure the practicability of the present application, this application further provides a specialized installation tool, as shown in FIGS. 9-11. The installation tool includes a screw implant tool for the pedicle screw 10, and a presser 29 for pressing the connecting claw 4 and the pedicle screw 10. In Embodiment 2, the locking screw 14 is not used, and thus a cross screwdriver 30 is provided for the threaded connecting between the connecting claw 4 and the screw seat 1.

The screw implant tool includes a tubular screwdriver 26 having a screw core 22. A fine thread is provided at a bottom of the screw core 22 and is configured to match with the internal thread of the blind hole. A first joint is provided at a top of the screw core 22 to connect to a core handle 28. The core handle 28 and the screw core 22 are detachably connected, or the core handle 28 is fixed to the first joint. A bottom of the tubular screwdriver 26 is provided with a connector to connect to the blind hole 12, and a hexagonal screwdriver is shown in the accompanying drawings as an example. A second joint is provided at a top of the tubular screwdriver 26 to connect to a tubular screwdriver handle 27. The tubular screwdriver handle 27 and the tubular screwdriver 26 are detachably or fixedly connected.

The bottom of the screw core 22 and the blind hole 12 of the spherical head 11 are in threaded connection. The tubular screwdriver 26 is sleeved on the screw core 22 to insert the connector at the bottom of the tubular screwdriver 26 into the blind hole 12. The tubular screwdriver handle 27 and the core handle 28 are sequentially installed and respectively fixed to the tubular screwdriver 26 and the screw core 22, which can realize the tight connection between the screw implant tool and the pedicle screw 10 and make the screw implant tool and the pedicle screw 10 coaxial, thereby holding and rotating the screw.

The presser 29 is a hollow circular plate provided with internal threads. At least two rotating handles are fixed in an outer surface of the circular plate. The presser 29 is able to rotate downward around the tubular screwdriver 26 to press the connecting claw 4 toward the spherical head 11 and realize the snap fit between the connecting claw 4 and the spherical head 11.

The cross screwdriver 30 is hollow and cylindrical and has a smooth inner surface. The cross screwdriver 30 is sleeved on the tubular screwdriver and is able to rotate around the tubular screwdriver. A least two rotating handles are fixedly provided in an outer surface of a top of the cross screwdriver, and the cross screwdriver having four rotating handles is shown in the accompanying drawings as an example. An outer surface of a bottom of the cross screwdriver is fixedly provided with a protrusion which matches with the cross groove 33 in the connecting claw 4.

The screw implant tool in Embodiments 1-3 is the tubular rotating tool 26 having the screw core 22. A fine thread is provided at a bottom of the screw core 22 and is configured to match with the internal thread of the blind hole. A first joint is provided at a top of the screw core 22 to connect to a core handle 28. The core handle 28 and the screw core 22 are detachably connected, or the core handle 28 is fixed to the first joint. A hexagonal screwdriver is shown in the accompanying drawings as an example, the screw core 22 has a bottom with fine threads and is screwed to the blind hole 12. The bottom 23 of the tubular screwdriver 26 is hexagonal and the top 25 of the tubular screwdriver 26 is provided with the second joint. The tubular screwdriver 26 is sleeved on the screw core 22 to insert the bottom 23 of the tubular screwdriver 26 into the blind hole 12. Next, the tubular screwdriver handle 27 and the core handle 28 are sequentially installed and fixed. The tubular screwdriver 26 and the pedicle screw 10 are firmly connected and coaxial. The pedicle screw 10 can be readily implanted, by the two rotating handles, into the pedicle where a screw track has been prepared.

Next, the core handle 28 and the tubular screwdriver handle 27 are firstly disassembled, and then the connecting claw 4 is sleeved on the tubular screwdriver 26 to abut against an upper surface of the spherical head 11. The presser 29 is screwed into an external thread at a middle rear part 24 of the tubular screwdriver 26 from the top 25 of the tubular screwdriver 26. Subsequently, the tubular screwdriver handle 27 and the core handle 28 are sequentially fixedly connected to the tubular screwdriver handle and the screw core. At this time, the presser 29 is rotated downward to readily press the connecting claw 4 downward, so as to allow the spherical cavity 7 to enclose the spherical head 11, thereby completing the connection between the connecting claw 4 and the pedicle screw 10.

Various installation methods are used in different embodiments.

For installing the pedicle screw assembly in Embodiment 1, the screw core 22, the tubular screwdriver 26 and the presser 29 provided on the tubular screwdriver 26 are disassembled. The screw seat 1 is screwed into the connecting claw 4. After all pedicle screw main bodies are assembled, the connecting rod 13 is installed and the locking screw 14 is used to pre-lock the screw seat 1. Then the plier of the screwdriver is stuck at the hole 32 to tighten the connecting claw 4, so as to complete the connection between the connecting claw 4, the screw seat 1 and the pedicle screw 10. Finally, the locking screws 14 are tightened in sequence to complete the installation.

For installing the pedicle screw assembly in Embodiment 2, the core handle 28, the tubular screwdriver handle 27 and the presser 29 are disassembled. The cross screwdriver 30 is sleeved on the tubular screwdriver 26 and inserted the cross groove 33 at the upper end of the inner cavity of the connecting claw 4. Then the tubular screwdriver handle 27 and the core handle 28 are respectively reconnected and are held to rotate cross screwdriver handles 31, so as to press the screw seat 1 downward. After the connecting rod 13 is installed, the connecting claw 4 is tightened to complete the fastening between the pedicle screw 10 and the connecting rod 13, thereby completing the installation of the pedicle screw rod system.

For installing the pedicle screw assembly in Embodiment 3, the screw core 22, the tubular screwdriver 26 and the presser 29 provided on the tubular screwdriver 26 are disassembled. The screw seat 1 is connected to the upper portion of the connecting claw 4. After the preliminary assembly of all the pedicle screw main bodies are completed, the connecting rod 13 is installed and the locking screw 14 is used to pre-lock the connecting claw 4. Then the plier of the screwdriver is stuck at the hole 32 to tighten the locking screw 14, so as to connect the screw seat 1, the pedicle screw 10 and the connecting rod 13 by the connecting claw 4, thereby completing the installation of the pedicle screw rod system.

The above descriptions are merely preferred embodiments of the present invention, and are not intended to limit the present application. Any modifications, replacements and improvements based on the spirit of the present application shall fall within the scope as defined by the appended claims.

What is claimed is:

1. A pedicle screw assembly for dynamic and static fixation, consisting of:
   a screw seat;
   a connecting claw; and
   a pedicle screw;
   wherein the connecting claw comprises an upper portion and a lower portion, which are integrated; the upper portion of the connecting claw is a hollow cylinder and is provided with an external thread on an outer surface of the upper portion of the connecting claw; the lower portion of the connecting claw is umbrella-shaped and is provided with a spherical cavity configured to adapt a spherical head of the pedicle screw; the lower portion of the connecting claw is equally divided into at least four petals; each petal is able to unfold outward by an external force; and an annular groove is provided on an outer surface of an intersection of the upper portion and the lower portion of the connecting claw;

a groove is provided on the screw seat to pass through a connecting rod; the screw seat is provided with a hollow cavity; a lower end of the screw seat is provided with an umbrella-shaped opening which adapts the lower portion of the connecting claw; an internal thread is provided at an upper portion of the hollow cavity of the screw seat to connect the upper portion of the connecting claw; and the spherical head of the pedicle screw has a flat top, which is perpendicular to an axis of the pedicle screw; a blind hole is provided in a center of the flat top of the spherical head and provided with an internal thread which matches with a screwdriver;

the screw seat comprises a cylindrical body and a hook for holding the connecting rod; the hook protrudes from a side of the cylindrical body; the cylindrical body and the hook are integrated; and the hook is provided with a hook body through which the connecting rod passes; and a recess is provided on an inclined surface of the lower portion of the connecting claw and is configured to cooperate with the hook body to lock the connecting rod between the hook body and the recess.

2. The pedicle screw assembly of claim 1, wherein the spherical cavity of the lower portion of the connecting claw and the spherical head of the pedicle screw are in clearance fit or interference fit; when the spherical cavity and the spherical head are in clearance fit, the lower portion of the connecting claw flexibly fixes the spherical head; when the spherical cavity and the spherical head are in interference fit, the lower portion of the connecting claw rigidly fixes the spherical head; and when the spherical cavity and the spherical head are in clearance fit, a width of the umbrella-shaped opening at the lower end of the screw seat is controlled to swing the pedicle screw within an angle of 10°.

3. The pedicle screw assembly of claim 2, wherein the clearance fit or interference fit between the spherical cavity and the spherical head depends on a height of the hook body or a diameter of the connecting rod.

\* \* \* \* \*